(12) United States Patent
Dijkstra (10) Patent No.: US 11,992,564 B2
(45) Date of Patent: May 28, 2024

(54) SYSTEM AND METHOD FOR STERILIZATION USING ADJUSTMENT IN DIRECTION OF ULTRA-VIOLET ILLUMINATION

(71) Applicant: FUTUREMEDIX, LLC, Longmont, CO (US)

(72) Inventor: Alain Dijkstra, Amstelveen (NL)

( * ) Notice: Subject to any disclaimer, the term of this patent is extended or adjusted under 35 U.S.C. 154(b) by 719 days.

(21) Appl. No.: 17/178,247

(22) Filed: Feb. 18, 2021

(65) Prior Publication Data

US 2021/0244837 A1 Aug. 12, 2021

Related U.S. Application Data

(63) Continuation-in-part of application No. 16/150,130, filed on Oct. 2, 2018, now Pat. No. 10,960,091.

(51) Int. Cl.
*A61L 2/10* (2006.01)
*A61L 2/24* (2006.01)

(52) U.S. Cl.
CPC .................. *A61L 2/10* (2013.01); *A61L 2/24* (2013.01); *A61L 2202/11* (2013.01); *A61L 2202/14* (2013.01); *A61L 2202/24* (2013.01); *A61L 2202/25* (2013.01)

(58) Field of Classification Search
CPC .......... A61L 2/10; A61L 2/24; A61L 2202/11; A61L 2202/14; A61L 2202/24; A61L 2202/25

See application file for complete search history.

(56) References Cited

U.S. PATENT DOCUMENTS

| 6,656,424 | B1 | 12/2003 | Deal |
| 9,517,280 | B2 | 12/2016 | Lynn et al. |
| 9,974,873 | B2 | 5/2018 | Cole |
| 2017/0246329 | A1 | 8/2017 | Lloyd |

*Primary Examiner* — Sean E Conley
(74) *Attorney, Agent, or Firm* — Willie Jacques; Emanus, LLC (57) ABSTRACT

The invention provides a UV illumination device for sterilizing and disinfecting a desired item or area. The UV illumination device comprises a base of a fixed housing. The base comprises a pair of electrical terminals establishing connection with external power source. A movable housing is connected to the fixed housing through a mechanical joint. The movable housing includes a plurality of light sources, a motor, an adjustment lens, a camera unit, a memory unit, and a controlling unit connected to the camera unit and the memory unit. The plurality of light sources, the camera unit, the memory unit and the controlling unit are mounted on a base plate. The controlling unit includes a processor configured to perform certain computing operations in order to control adjustment in the direction of UV illumination by the UV illumination device.

15 Claims, 10 Drawing Sheets

SYSTEM AND METHOD FOR STERILIZATION USING ADJUSTMENT IN DIRECTION OF ULTRA-VIOLET ILLUMINATION

CROSS-REFERENCE TO RELATED APPLICATIONS

This application is a continuation-in-part application of U.S. non-provisional application Ser. No. 16/150,130, filed Oct. 2, 2018, claiming priority from this same U.S. non-provisional application Ser. No. 16/150,130, filed Oct. 2, 2018, the entire contents of which are incorporated herein by reference.

FIELD OF THE INVENTION

The present invention relates generally to a device and method for Ultraviolet (UV) disinfection of physical objects. More specifically, the device providing UV disinfection or sterilization to a bathroom, hospital room, toilet, door handle, and all other areas which need to be sterilized and disinfected with UV radiation. Still more specifically, the present invention relates to a device and a method for sterilization of physical objects by utilizing adjustment in direction of ultra-violet illumination.

DESCRIPTION OF THE BACKGROUND ART

Different forms of light can be used in different applications by making use of specific wavelengths of light effects such as inactivation of bacteria, fungi, viruses, chemical reactions including the curing of plastics and other materials.

Historically, mercury lamps have been the only option for disinfection and sterilization. But with UV LED technology advances, there are new options that are smaller, more robust, toxin-free, long-lived, energy-efficient, and allow infinite on/off switch mechanism. The UV LED technology allows solutions to be smaller and portable, battery-powered, and with the instant full light output.

Ultraviolet (UV) light has been used for many years in the industry, particularly in, health and hygiene regimes.

As known in the art, Ultraviolet (UV) radiation emitted at certain wavelengths is mutagenic to micro-organisms. Sub-type C of the UV spectrum (UVC), also referred to as "germicidal" UV radiation, is generally considered to be radiation emitted at a wavelength ranging from 100-280 nanometers. On application, the UVC radiation can be used to inactivate (i.e., destroy, render harmless, and/or prohibit the growth or reproduction) certain micro-organisms.

Prevention of infection by certain micro-organisms is an important concern in places where micro-organisms are substantially present like laboratory settings, gyms, hospitals, locker rooms, and bathrooms, etc. In a hospital operating room, for example, it may be important to inactivate microorganisms at the surgical site and on surfaces in the operating room, such as the operating table. This is often accomplished through the use of specialized UV lamp fixtures surface-mounted on the ceiling of the operating room. Also, specialized UV lamp fixtures are often mounted in the ceilings of an operation theatre in hospitals, to disinfect the OT apparatuses.

In the U.S. Pat. No. 6,656,424B1 Jeffery L. Deal discloses an Ultraviolet Area Sterilizer (UVAS) which is mobile or stationary. The UVAS is positioned in a room, such as an operating room or intensive care unit. Motion detectors sense movement, to assure that personnel have evacuated the space to be sterilized. Subsequently, UV-C generators, such as a bank of mercury bulbs, generate intense levels of UV-C. An array of multiple UV-C sensors scans the room and determines the darkest area, or the area reflecting the lowest level of UV-C back to the sensors. A basic Stamp contained in the device calculates the time required to obtain a bactericidal dose of UV-C reflected back from the darkest area. Once a bactericidal dose has been reflected in all the sensors, the unit notifies the operator and shuts down. By relying on reflected doses rather than direct exposure, the UVAS can sterilize or sanitize all surfaces within the room that are within view of an exposed wall or ceiling.

In another U.S. Pat. No. 9,517,280B2, William Warren Lynn et.al, discloses a germicidal light fixture and germicidal light fixture system. The germicidal light fixture includes a support structure and at least one first lighting device coupled with the support structure operative to emit ultraviolet radiation at a first predetermined wavelength. At least one-second lighting device is coupled with the support structure and is operative to emit ultraviolet radiation at a second predetermined wavelength. The first and second predetermined wavelengths are selected such that ultraviolet radiation emitted from at least one first lighting device and the at least one second lighting device, respectively, is operative to inactivate microorganisms. At least one-third of the lighting device is coupled with the support structure and is operative to emit visible radiation.

In another U.S. Pat. No. 9,974,873B2 Theodore John Cole, discloses a germicidal system for use in disinfecting a human interface device includes at least one human interface device. One or more ultra-violet (UV) light sources are used in proximity to the at least one human interface device for disinfecting a touch surface of the human interface device below surgical grade sterilization. A memory for storing user data of the at least one UV light source. At least one server is used for providing a central storage location for user data supplied from the memory and a computer is used in communication with at least one server for controlling the operational parameters of at least one UV light source.

The existing devices mentioned above though involves the application of UV radiation to be emitted on the area or on to the item to be disinfected or sterilized, but the setting of the orientation of the UV light to adjust the light to project it on the surface or item to be sterilized or disinfected is not achieved by these mentioned existing devices or any UV light illumination device developed till present. Hence, in view of this, there is a need for a light illumination device or a light source that facilitates adjustment of the light on the area or item to be sterilized.

The existing devices are not compact enough and are only limited to one type of UV radiation which is not effective for complete disinfection and sterilization. The existing devices have multiple parts making the product bulkier and costlier. Further, the existing devices are not capable of object detection and/or material identification for disinfection and sterilization.

Hence, it is desirable to have a device that is smart enough to sense the human presence, identify different materials, and provide the UV light projection based on the properties of the different materials.

Further, it is still desirable to have a device that can fit with the existing lighting fixtures and doesn't require any special arrangement for installation.

BRIEF SUMMARY OF THE INVENTION

The summary of certain example embodiments provided below are disclosed by way of example and are not intended to be limiting. References to "one embodiment," "at least one embodiment," "an embodiment," and so on indicate that the embodiment(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment According to one aspect of the present disclosure, the light projection unit includes a light head, a light direction controller, and a UV light source. Further, the UV light source is adapted to project a UV light to the light direction controller which can adjust the direction of the light projection in any desired direction and passes it through the light head.

According to another aspect of the present disclosure, the light direction controller could be a galvanometer, a laser sintering device, a saccade mirror, a direction tuning film, or any other device that can control the direction of the light projection.

According to yet another aspect of the present disclosure, the controlling unit is operably connected to the camera unit, the memory unit, and the light projection unit. Further, the controlling unit includes a processor that is adapted to execute computer implemented code stored in the memory unit to control the camera unit, the memory unit and the light projection unit.

Further, the controlling unit is adapted to use an object detection module, localization module, machine learning module, and artificial intelligence module to identify at least one item within the enclosed area, wherein the enclosed area could be a bathroom, a toilet, an operation theater or any other closed structure needs to be sterilized and disinfected.

According to yet another aspect of the present disclosure, the UV illumination device is adapted to identify the presence of a living organism e.g., a human, an animal, a pet, etc., by using the object detection, localization module, and artificial intelligence and machine learning module. Further, the controlling unit utilizes the camera unit to identify the presence of a living organism. Upon detection of the human presence, the UV Illumination device is adapted to illuminate only the normal light e.g., white household light.

According to yet another aspect of the present disclosure, the memory unit has pre-stored information related to various materials, sizes, shapes, color, texture, etc. helping the UV illumination device to identify the objects and/or materials that needs to be treated with the UV light projection and the objects and/or materials which needs to be prevented from the UV light projection.

According to yet another aspect of the present disclosure, the UV illumination device may be of different shapes and sizes to fit in a conventional light bulb holder, a tube light holder, and/or a table lamp, etc.

According to yet another aspect of the present disclosure, to use the UV illumination device, the user mounts the UV illumination device in the conventional light holder. The UV illumination device is adapted to activate the camera unit to scan at least one item in the enclosed area and the controlling unit identifies the scanned item by using the localization module, the object detection module, the artificial intelligence module, and the machine learning module. Further, the controlling unit is adapted to categorize and list the identified items based on their parameters. Further, the identified items are prioritized based on the frequency of their use. The controlling unit can automatically control the intensity, time, and shape of the UV light beam based on the parameters of the prioritized item, and projects the UV light beam on the item or object to be disinfected or sterilized.

According to yet another aspect of the present disclosure, the UV illumination device is connected to a remote device via a communication means. The communication means can be a wired or wireless connection between the remote device and the UV illumination device. Further, the UV illumination device may receive user input via the remote device and displays the captured images and videos on the remote device. Further, the user can manually identify, select, prioritize at least one item to be sterilized and disinfected based upon his/her intellect by using the remote device. Furthermore, the user can control the shape, time, and intensity of the UV light beam based on the parameters of at least one item by using the remote device.

According to yet another aspect of the present disclosure, the UV illumination device is having a rotation means to project the UV illumination in all possible directions. Further, the UV illumination device is compact in size and easily portable. The UV illumination device operates under many mechanisms, for example, intended but not limiting to locking joint mechanism, hinge mechanism, spherical rolling joint mechanism, pan and tilt mechanism, ball socket mechanism, or any other locking mechanism.

Additionally, the UV illumination device of the present invention allows detection of human presence, identification of different materials, and providing of the UV light projection based on the properties of the different materials.

In one embodiment, the device comprises a fixed housing including a base and a movable housing. The base comprises a pair of electrical terminals establishing a connection with an external power source. The movable housing is connected to the fixed housing through a mechanical joint. The movable housing includes a plurality of light sources, a motor, an adjustment lens, a camera unit, a memory unit, and a controlling unit connected to the camera unit and the memory unit. The controlling unit includes a processor configured to perform the following steps including initiating the camera unit to scan at least one item within an enclosed area; storing a scanned data of at least one item in the memory unit; identifying at least one item from the scanned data; rotating the motor which in turn facilitates the rotation of the UV illumination device, illuminating UV light on at least one item identified from the scanned data, projecting the UV light on the at least one item, providing back and forth movement to the adjustment lens with respect to the plurality of light sources using the motor and adjusting the UV light illuminated on the at least one item.

Further, the plurality of light sources, the camera unit, the memory unit, and the controlling unit are mounted on a base plate. The mechanical joint is attached to a support surface in a rotatable manner. The mechanical joint further comprises a socket accommodating a ball in a manner that the ball can rotate in any desired direction within the socket. The plurality of light sources could be a plurality of light-emitting diode (LED), laser lights, or any other light sources which can produce light in the UV range. The movable housing further comprises a transparent cover to cover the base plate and is mounted on the support surface.

In yet another embodiment, the UV illumination device is made waterproof and is also able to work under the water surface to sterilize or disinfect water.

The foregoing has outlined rather broadly the features and advantages of the present invention so that the detailed description of the invention that follows may be better understood. Additional features and advantages of embodiments of the invention will be described hereinafter which form the subject of the claims of the invention. The conception and specific embodiment disclosed herein may be readily utilized as a basis for modifying or designing other structures for carrying out the same or similar purposes of the present invention. Please note that such equivalent constructions do not depart from the scope of the invention as set forth in the appended claims. The novel features which are characteristic of the invention, both as to its organization and method of operation, together with further objects and advantages, will be better understood from the following description when considered in connection with the accompanying figures. Each of the figures is provided for the purpose of illustration and description only and is not intended as a limitation of the scope of the present invention or appended claims.

DETAIL DESCRIPTION OF THE DISCLOSURE

Embodiments of the present disclosure will be described more fully hereinafter with reference to the accompanying drawings in which like numerals represent like elements throughout the figures, and in which example embodiments are shown.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context necessitates otherwise. Structures described herein are to be understood also to refer to functional equivalents of such structures. The language that may be construed to express approximation should be so understood unless the context dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will now be described in detail with reference to embodiments thereof as illustrated in the accompanying drawings.

From reading the present disclosure, other variations and modifications will be apparent to persons skilled in the art. Such variations and modifications may involve equivalent and other features that are already known in the art, and which may be used instead of or in addition to features already described herein.

References to "one embodiment," "an embodiment," "various embodiments," etc., may indicate that the embodiment(s) of the invention so described may include a particular feature, structure, or characteristic, but not every embodiment necessarily includes the particular feature, structure, or characteristic. Further, repeated use of the phrase "in one embodiment," or "in an embodiment", "another embodiment," does not necessarily refer to the same embodiment, although they may.

As it is well known to those skilled in the art many careful considerations and compromises typically must be made when designing for the optimal manufacture of a commercial implementation of any system, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

A memory unit includes, but is not limited to, a hard drive, compact disc, flash memory, volatile memory, random access memory, magnetic memory, optical memory, semiconductor-based memory, phase change memory, optical memory, periodically refreshed memory, and the like; however, the non-transitory computer readable medium does not include a pure transitory signal per se.

Figure 1:
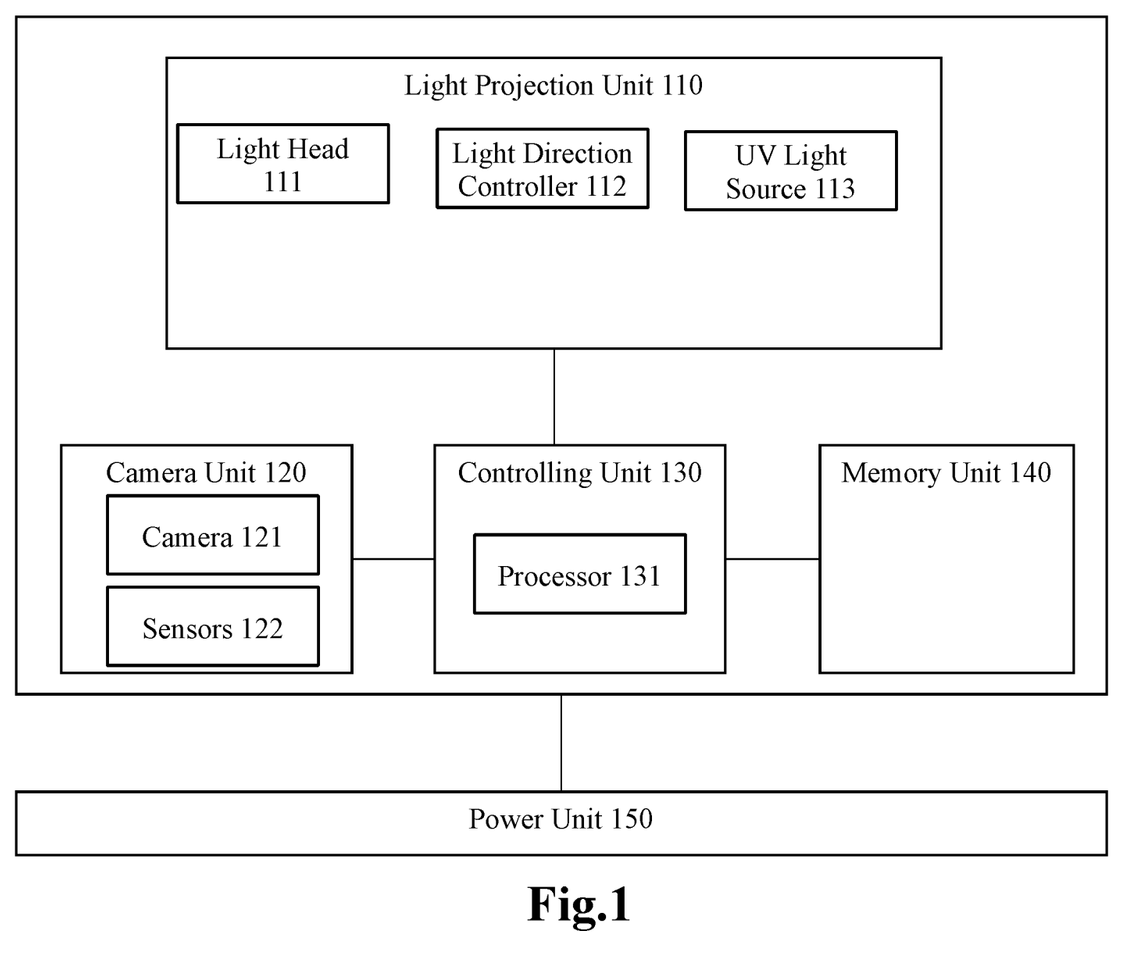
FIG. 1 shows a block diagram of the components of a UV illumination device according to an embodiment of the present disclosure.

Referring to FIG. 1 shows a block diagram of a UV illumination device 200 according to an embodiment of the present disclosure. The UV illumination device 200 includes a light projection unit 110, a camera unit 120, a controlling unit 130 a memory unit 140, and a power unit 150. Further, the light projection unit 110 includes a light head 111, a light direction controller 112, and a UV light source 113 which is adapted to project the UV light (not shown) on the light direction controller 112, thereafter the light direction controller 112 directs the UV light in the desired direction through the light head 111. Further, the light projection unit 110 also includes a rotation motor that can rotate the light head 111 in any desired direction based upon the controlling unit 130 input.

The UV illumination device 200 uses a mirror galvanometer as the light direction controller. In this, the galvanometer consists of a coil that is suspended using silken threads. At least one mirror is attached to at least one coil. The light from the light source is made to fall on one mirror. The reflected light will fall on a light head 111 to project the light on the desired area. When the coil deflects the mirror deflects with it. The light which is deflected also moves on the desired surface. The distance on the desired surface determines the sensitivity of the galvanometer. As the distance increases, the deflection of the light even for a small current will be large. Thus, the even low value can be measured with high precision. Wherein, the light direction controller 112 could use a mirror galvanometer, a laser sintering device, saccade mirror, and direction tuning film or any other device that can control the direction of the light projection.

The controlling unit 130 is electronically and communicatively coupled to the light projection unit 110, the memory unit 140, the camera unit 120, and the power unit 150. In this, the processor 131 is adapted to control the light projection unit 110 based on the camera unit 120 inputs.

Further, the camera unit 120 includes a camera 121 and a plurality of sensors 122. The camera unit 120 is configured to scan at least one item and store a scanned data of at least one item in the memory unit 140. Further, the plurality of sensors 122 are adapted to sense the motions of at least one item and identify parameters of said at least one item, wherein the memory unit 140 includes a pre-stored information related to a structure, material, shape, size, intensity, and time required for sterilization and disinfection, etc. for a particular metal or material. Further, the controlling unit 130 compares the parameters of said at least one item with the pre-stored information stored in the memory unit 140 to identify said at least one item.

According to an embodiment of the present disclosure, the camera unit 120 is an IP (internet protocol) camera that can rotate at 0 degree-360-degree angle to broaden the scanning area coverage.

Figure 2:
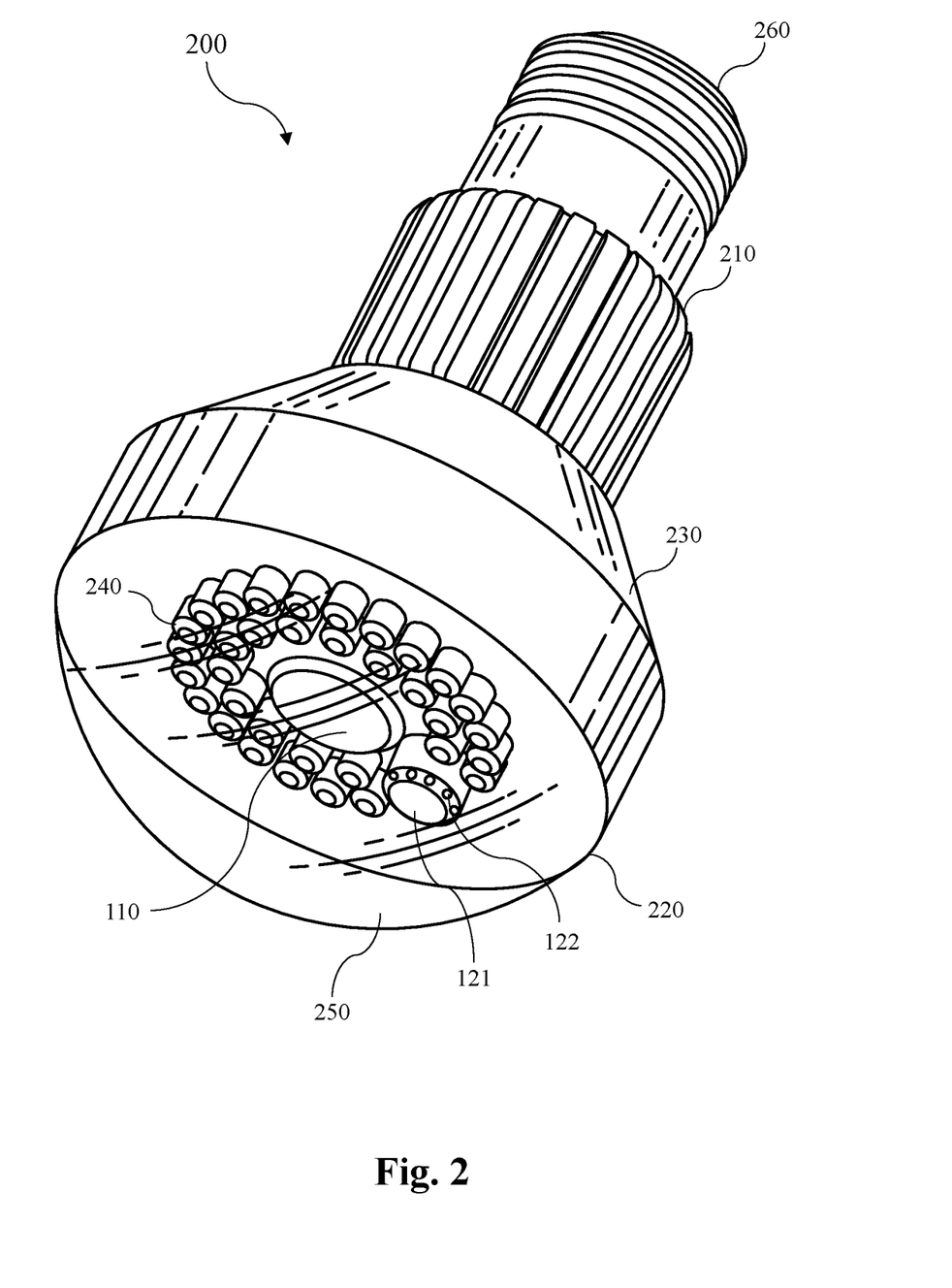
FIG. 2 shows an isometric view of the UV illumination device according to an embodiment of the present disclosure.
Figure 3:
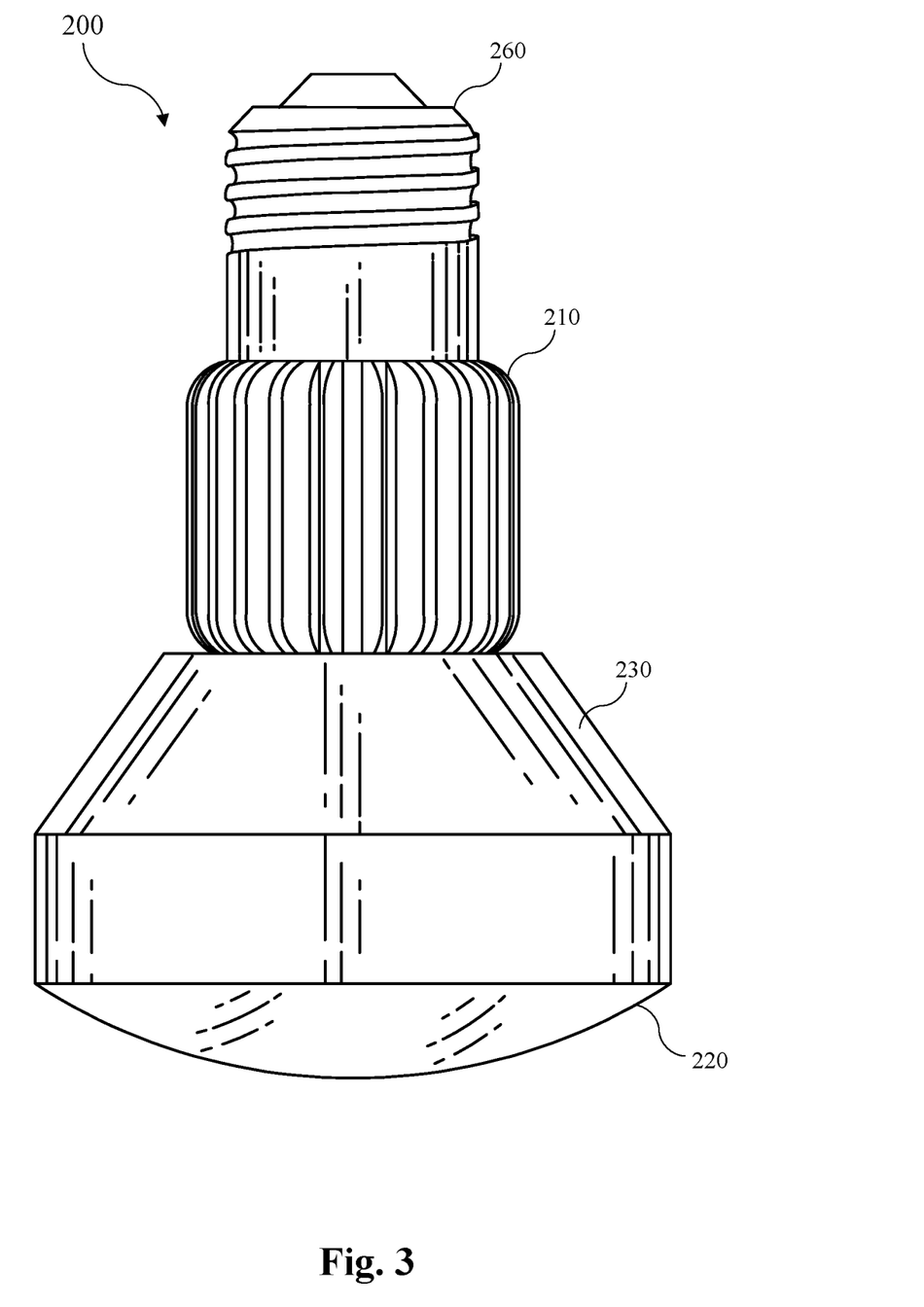
FIG. 3 shows a plan view of the UV illumination device according to an embodiment of the present disclosure.

Further, the UV illumination device 200 in the shape of a conventional bulb is shown in FIG. 2 and FIG. 3 according to an embodiment of the present disclosure. In this embodiment, the device 200 has a shell body 230 which includes the light projection unit 110 and the camera unit 120. Further, the shell body 230 has a front end 220 and a rear end 210. The front end 220 of the shell body 230 is covered by a transparent cover 250.

The shell body 230 accommodates the light projection unit 110 and the camera unit 120 at the front end 220 and a base 260 is attached at the rear end 210. Further, the light projection unit 110 and the camera unit 120 are substantially encircled by a plurality of LEDs 240 at the front end 220 of the shell body 230. Wherein, the shell body 230 also contains the controlling unit 130 and the memory unit 140.

Further, the light projection unit 110, the camera unit 120, the memory unit 140, the controlling unit 130, and the plurality of LEDs 240 that accommodated within the shell body 230 having an appropriate shape and dimensions, and positive and negative electrical contacts (not shown) to get power from the power unit 150, wherein the power unit 150 can be an external power source or a battery within the UV illumination device 200. Further, when the electrical contacts connect with the power source and the power source is thereby connected to the desired electric parts and accessories. Further, base 260 has positive and negative terminals to connect the UV illumination device 200 to the external power source.

Figure 4:
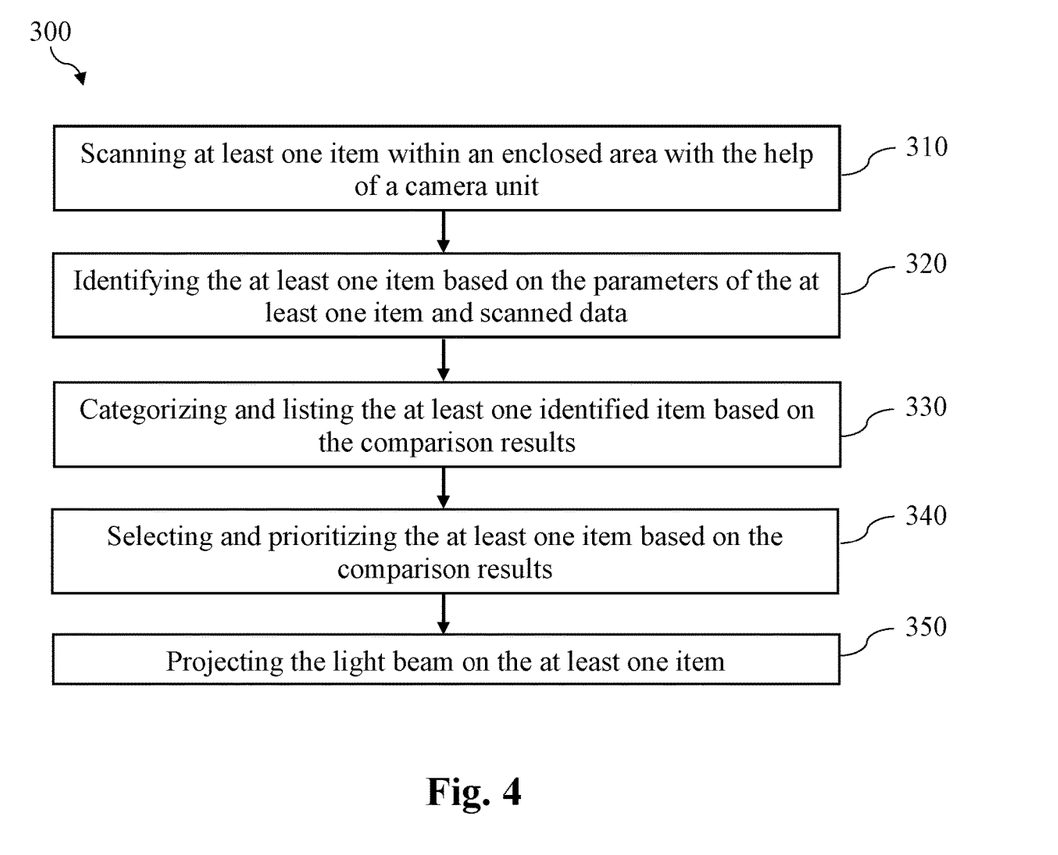
FIG. 4 shows a flowchart of the UV illumination process according to an embodiment of the present disclosure.

Referring to FIG. 4, a flowchart 300 shows the UV illumination process according to an embodiment of the present disclosure, wherein the user switches ON the power supply, thereby activating the controlling unit 130. Thereafter, the controlling unit 130 is adapted to activate the camera unit 120 and direct the camera unit 120 to start scanning an enclosed area to be disinfected or sterilized. Camera 121 scans at least one item within the enclosed area at step 310, the plurality of sensors 122 collects the parameters of said at least one item. The memory unit 140 receives the parameters of said at least one item and a scanned data from the camera unit 120. At step 320, the controlling unit 130 automatically identifies said at least one item by comparing the parameters of said at least one item and scanned data with the pre-stored information stored in the memory unit 140 by using the artificial intelligence module, localization module, machine learning module, and object detection and founds the parameter of the at least one item in the pre-stored information of the memory unit 140. Further, at step 330 the controlling unit 130 categorizes and lists said at least one item based on comparison results. The controlling unit 130 uses artificial intelligence and machine learning module to automatically prioritize and select said at least one item based on the comparison results at step 340. Furthermore, the controlling unit 130 based on the artificial intelligence and machine learning modules allows the light projection unit 110 to project the UV light beam 114 on said at least one item at step 350. Wherein, if the parameters of said item not found in the pre-stored information of the memory unit 140 the device avoid projecting UV light said item or a user via a remote device can manually provide the information related to said item and the controlling unit 130 allows the light projection unit 110 to project light on the said item for a user-defined period and intensity. Wherein the remote device can be a mobile phone, a touchscreen displays, a computer, a laptop, a remote control or any other suitable device allows to view the scanned data and enter user input.

According to an alternate embodiment of the present invention, the user can manually perform the sterilizing and disinfecting operation on the UV illumination device 200. In this, the user establishes a connection between the remote device and the UV illumination device 200 via communication means i.e., wired or wireless connection means. The remote device is having a user interface where the user can see the scanned data from the camera unit 120 and provides input to the controlling unit 130 to scan the enclosed area with the help of the camera unit 120. Further, the user selects an item and categorizes the items based on the parameters of said item. After categorizing the items, the user can make a list of the identified and categorized items on the remote device. Thereafter, the user is adapted to prioritize the list based on the frequency of their use and the parameters via using the user interface of the remote device. Further, the remote device sends the prioritized list of the items to the controlling unit 130 and the controlling unit 130 having the processor 131 instructs the light projection unit 110 to project the UV light based on the prioritized list of the items. This is achieved by controlling the UV illumination device 200 via a mobile phone, a mobile application, a laptop, a remote control, an IP-controlled camera, or any other device which allows a user to identify and select a desired treatment area for the UV illumination.

According to an embodiment of the present disclosure, the controlling unit 130 is having artificial intelligence and machine learning module, localization, and object detection module for the automatic functioning of the UV illumination device. The controlling unit 130 uses these modules for automatically selecting, identifying, prioritizing various objects or items and provides UV treatment automatically based on the predefined parameters of the object or item.

According to an embodiment of the present disclosure, the localization module provides a complete visual module to localize objects using the camera unit 120. The localization module requires a preprocessing algorithm to segment a scene into objects. Ideally, the preprocessing algorithm should be able to segment an unstructured scene into objects using visual cues such as shape, texture, edges, and color in real-time.

Further, the object detection module provides a way to identify specifically trained objects within the current image. Once the module is trained with sample template images it will identify those objects within the current image depending on the filtered parameters of confidence, size, rotation, etc.

Furthermore, the UV illumination device 200 also uses machine artificial intelligence and learning algorithms to estimate a predictive model that best generalizes to a particular type of data. Therefore, for solving a problem by machine learning and artificial intelligence, it is imperative to have a large number of examples that can be used by the learning algorithm to understand the system's behavior and similar kind of predictions can be generated by the system when the machine learning algorithm is presented with new examples of data. The system records and learns various methods of treatment used by the user or by the UV illumination device 200 for different objects or items. e.g., if a user uses UV light of a particular intensity and shapes for sterilizing a particular item the device uses artificial intelligence and machine learning module to learn and record all the events that happened during the treatment and in the future, if the UV illumination device 200 is presented with the same item it uses its learning from the previous similar treatment and can automatically provide treatment based on its learning.

Figure 5:
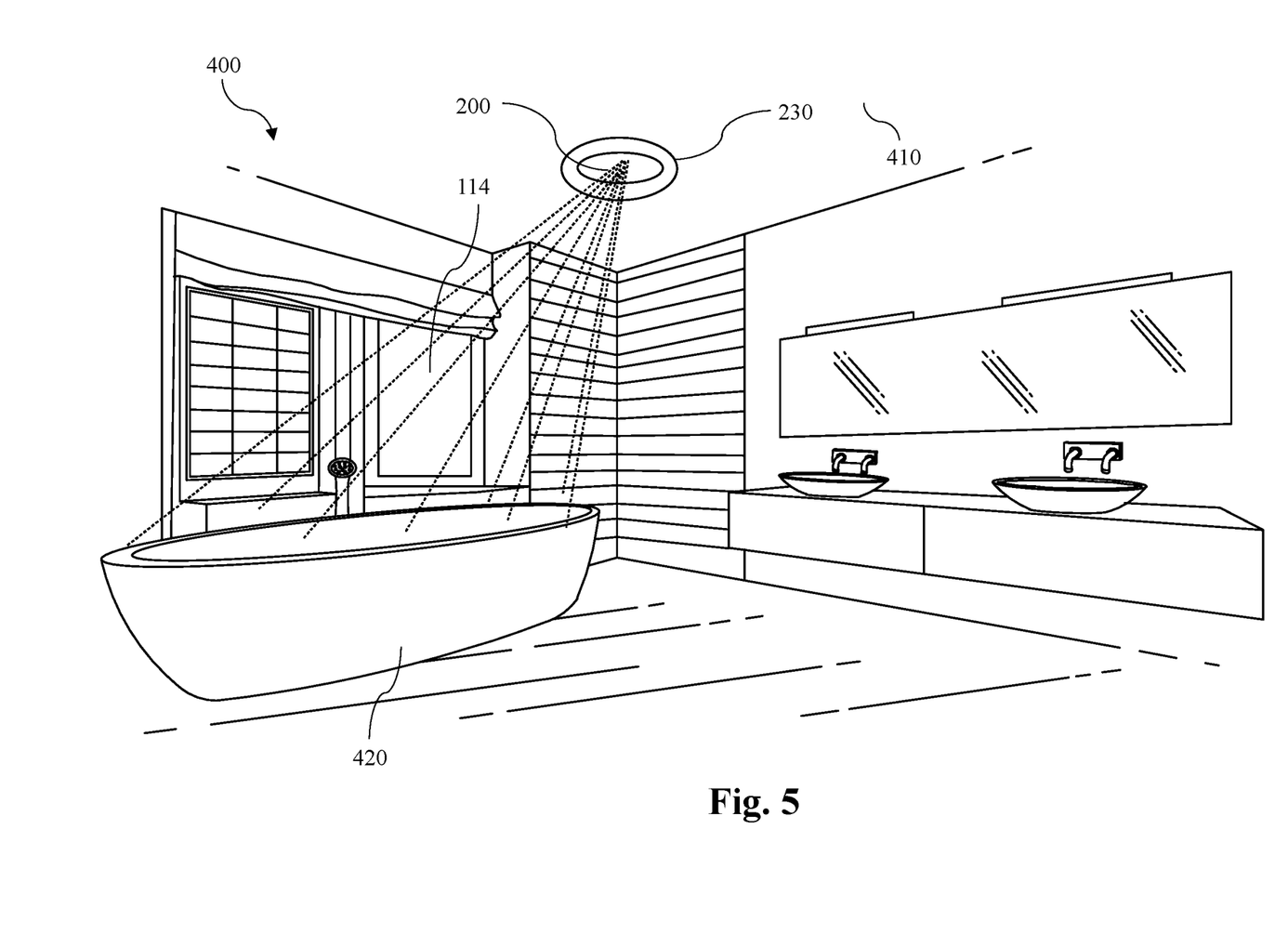
FIG. 5 shows the UV illumination device used in a bathroom according to an embodiment of the present disclosure.

Referring to FIG. 5, shows the configuration of the UV illumination device 200, in a bathroom 400 according to an embodiment of the present disclosure. In this, the UV illumination device 200 is fixed in a conventional light holder 430 mounted on ceiling 410 of the bathroom 400. The UV illumination device 200 projecting the UV light beam 114 on a bathtub 420 for disinfecting and sterilizing the bathtub 420.

Figure 6:
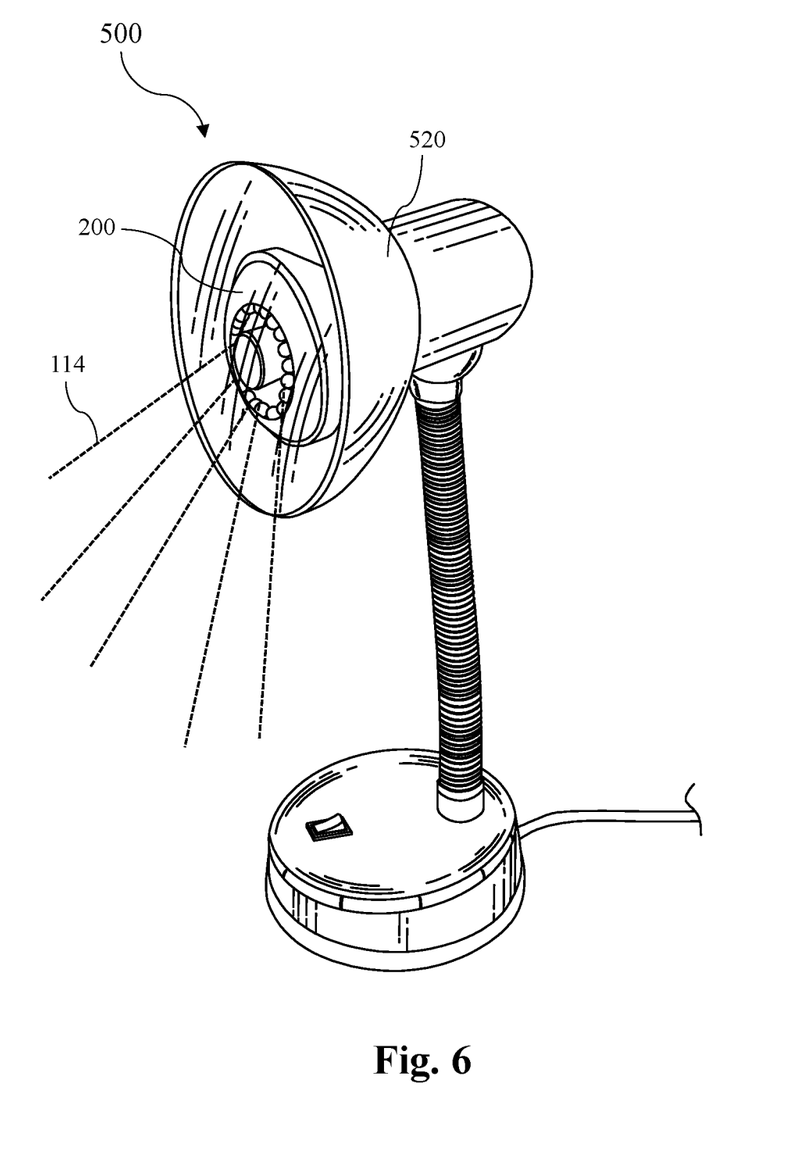
FIG. 6 shows the UV illumination device in a lamp fixture according to an embodiment of the present disclosure.

Referring to FIG. 6 shows the configuration of the UV illumination device 200 in a table lamp 500 according to an embodiment of the present disclosure. The UV illumination device 200 is mounted inside a table lamp holder 520 of the table lamp 500 and projecting the UV light beam 114.

Figure 7:
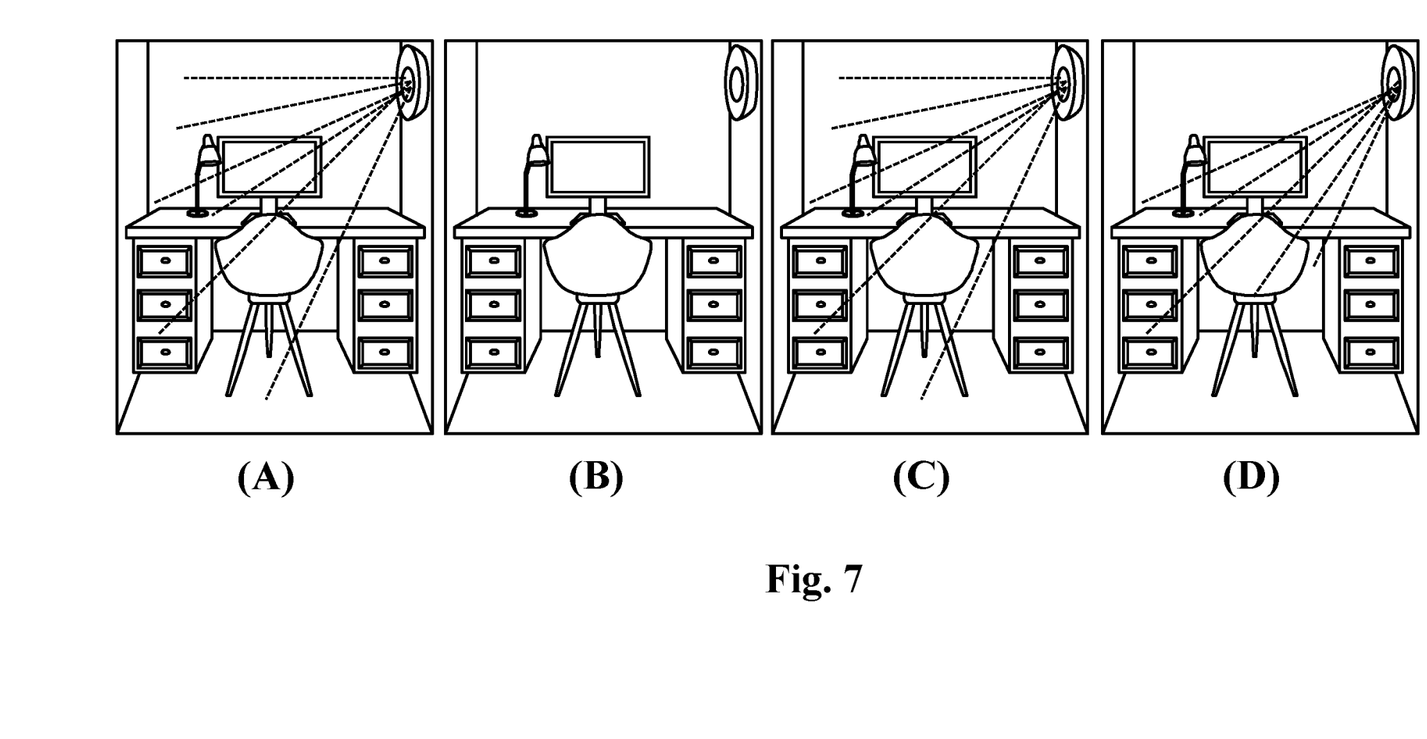
FIG. 7 shows the various operations performed by the UV illumination device based on the circumstances according to an embodiment of the present disclosure.

Referring to FIG. 7 shows various operations performed by the UV illumination device 200 based on the circumstances in the enclosed area according to an embodiment of the present disclosure. The UV illumination device 200 is mounted on the sidewall of a room. Further, the UV illumination device 200 is responding according to various situations occurring in the room as follows:

According to situation 'A', the UV illumination device 200 is illuminating the normal household light. The situation 'A' occurs only when, a person, a pet, or any other living organism is present in the room or the door of the room is open.

According to situation the UV illumination device 200 is not illuminating any light, this situation occurs when the user just exited the room and the illumination device stops illuminating the normal light.

According to situation 'C', the UV illumination device 200 is scanning the room and identifying the objects or items which need to be disinfected or sterilized based on the frequency of their use and their parameters.

According to situation To', the UV illumination device 200 is projecting the UV light on the identified item or object i.e., table as shown in the situation 'D'.

Figure 8:
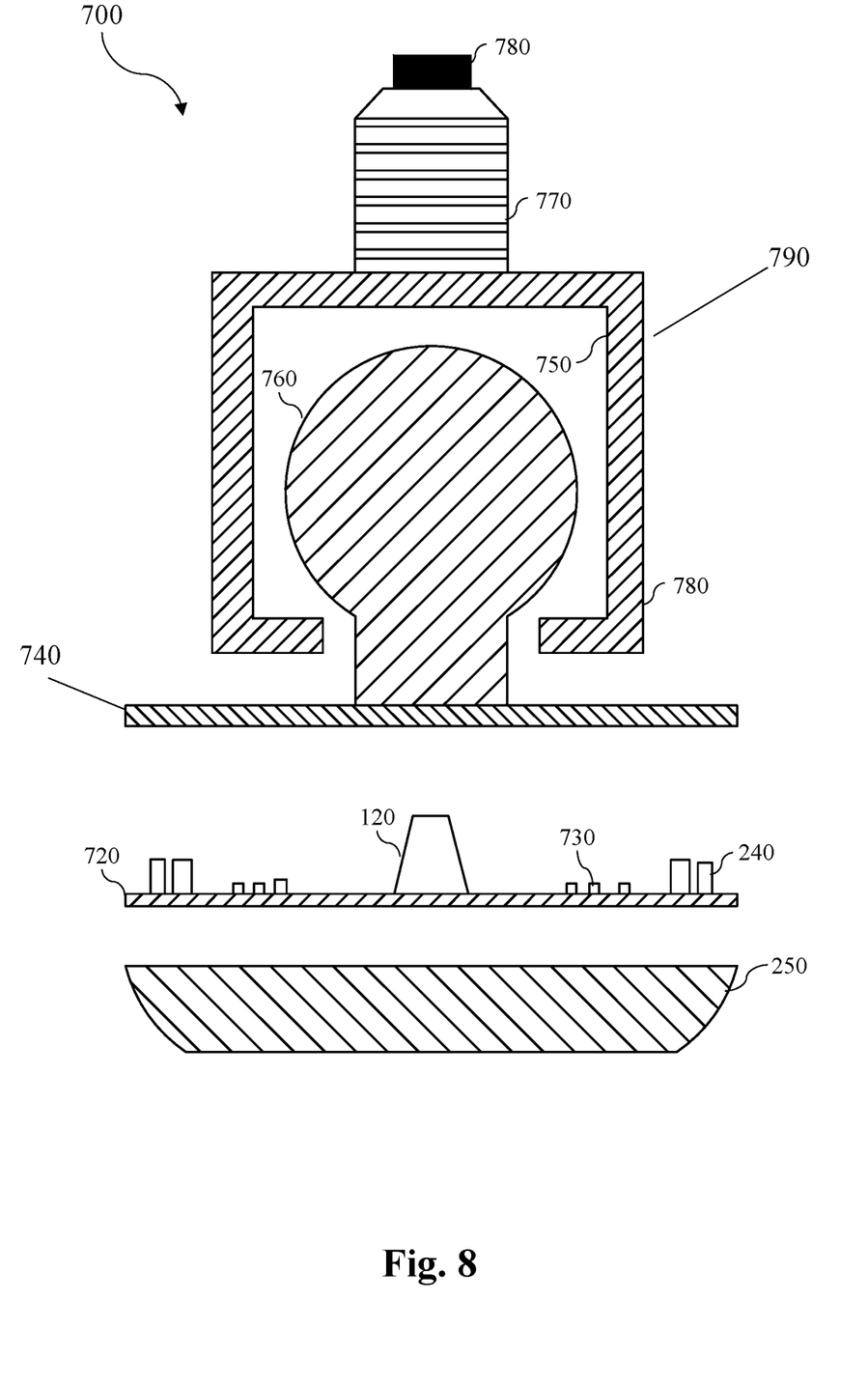
FIG. 8 shows an exploded view of a UV illumination device according to another embodiment of the present disclosure.

Referring to FIG. 8, an exploded view of a UV illumination device 700 is shown according to another embodiment of the present disclosure. In this embodiment, the plurality of LEDs 240, the camera unit 120, the memory unit 140 (not shown), the controlling unit 130 (not shown), and other required electrical or electronic components 730 are mounted on a base plate 720. The transparent cover 250 is covering the base plate 720 and mounted on a support surface 740, wherein the transparent cover 250 is made of glass, plastic, or any other suitable transparent material. Further, the support surface 740 is attached to a rotation assembly 790 in a rotatable manner, the rotation assembly 790 is a ball-socket joint in which a socket 750 is accommodating a ball 760 in a manner that the ball 760 can rotate in any desired direction within the socket 750. Furthermore, a base 770 which is a conventional bulb base is attached to the socket 750 and the base 770 is having electrical terminals 780 to establish an electrical connection with the external power source via a conventional bulb holder. Furthermore, the rotation assembly 790 is having a rotation motor (not shown) that is controlled by the controlling unit 130 (not shown) mounted on the base plate 720 to rotate the UV illumination device 700 in any desired direction. The controlling unit 130 is using an artificial intelligence module, machine learning module, object detection module, and localization module to automatically scanning the enclosed area, identifying at least one item, selecting at least one item, prioritizing at least one item, rotating the UV illumination device 700 and illuminating the UV light on the selected and prioritized object or item. The plurality LEDs 240 are acting as UV light source 113 when the UV illumination device 700 starts sterilizing and disinfecting function.

According to an alternate embodiment of the present disclosure, the UV illumination device (200, 700) is having a light source for producing UV light e.g., LEDs, UV lamps, arc welding, laser light, mercury vapors lamps, and all other UV light sources proving light in the UV range.

According to an alternate embodiment of the present disclosure, the UV illumination device (200, 700) can use another rotation mechanism e.g., cam mechanism, gear mechanism, or any other suitable rotation mechanism.

According to an alternate embodiment of the present disclosure, the enclosed area can be a room, a toilet, an operation theater, a lift, or any other desired area to be disinfected and sterilized.

According to an alternate embodiment of the present disclosure, at least one item within the enclosed area can be a floor, a tub, a door handle, a washbasin, a toothbrush, or any other desired item.

According to an alternate embodiment of the present disclosure, the priority of the selected item is decided based on the frequency of the use, in detail the item which is used more often would be more prone to germs hence would be treated first. In this, the device can automatically decide the priority of the treatment or the user can manually decide the priority for the treatment by using a remote device.

According to an alternate embodiment of the present disclosure, the UV illumination device (200, 700) can illuminate the UV light based on the predefined parameter of the object or item to be sterilized or disinfected. The device can produce UV-A, UV-B, UV-C, etc. type radiations as per the requirement. Table below describes the various types of UV radiation with their wavelength and property.

the parameters of at least one item or object to be sterilized or disinfected e.g., shape, size, structure, material, metal, plastic, intensity, and time required for disinfection and sterilization, size and shape of the light beam, etc. so that when the camera scan an item the device already have all the information related to that item and the UV illumination device (200, 700) can automatically start the treatment based on the pre-stored information by using an artificial intelligence module, machine learning module, and object detection module. Further, in case the UV illumination device (200, 700) doesn't have the information related to the scanned item the user can manually provide the input of the item, and the UV illumination device (200, 700) uses a machine learning module to store the information provided so that in future the UV illumination device (200, 700) can easily identify the item and can provide the treatment without user intervention.

Figure 9:
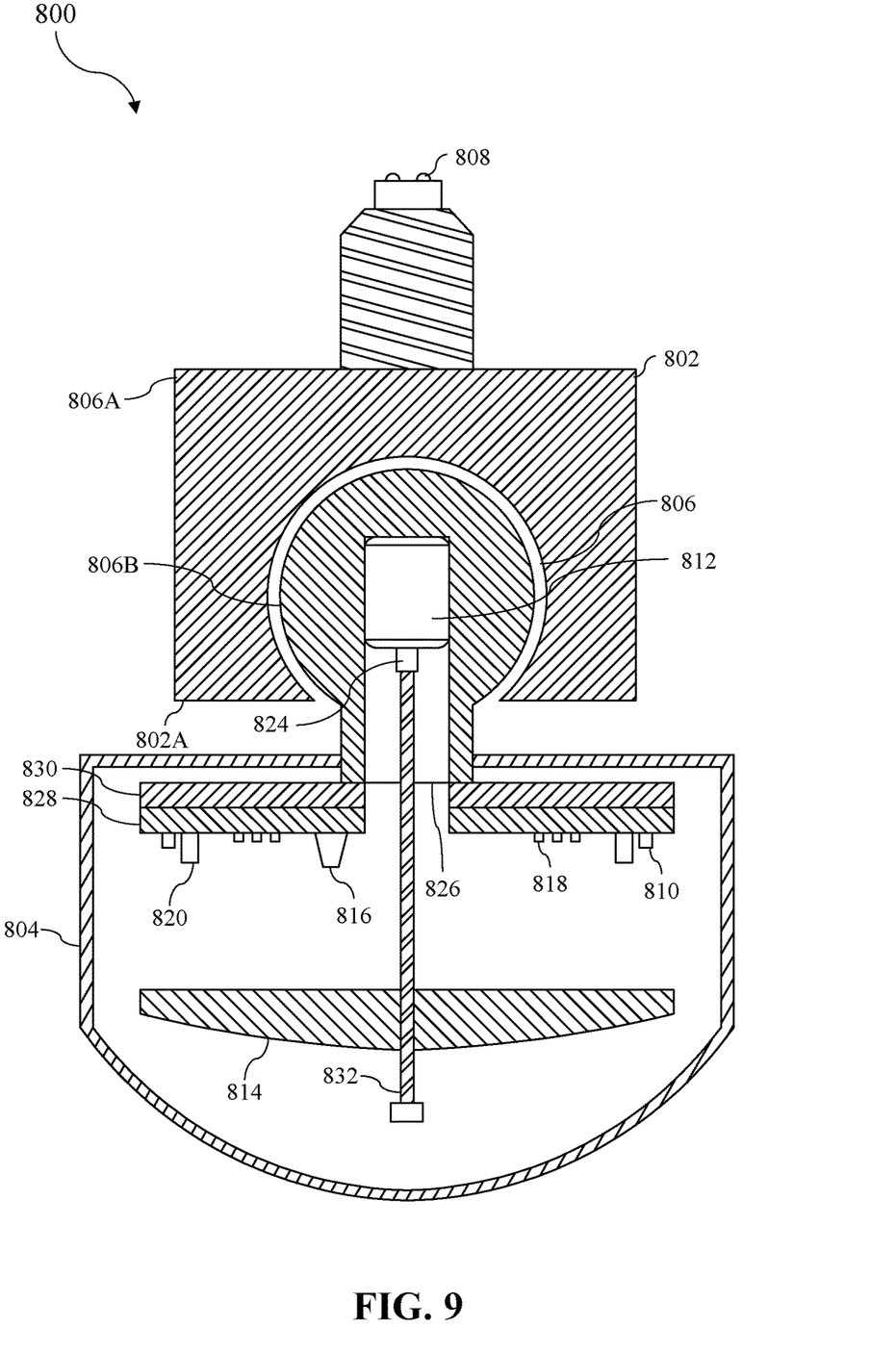
FIG. 9 shows the configuration of the UV illumination device according to an alternate embodiment of the present disclosure; and, FIG. 10 shows a block diagram of the components of a UV illumination device according to an alternate embodiment of the present disclosure.

FIG. 9 illustrates a configuration of the UV illumination device according to an alternate embodiment of the present disclosure The UV illumination device 800 comprises fixed housing 802 including a base 802A and a movable housing 804. The base 802A comprises a pair of electrical terminals 808 establishing a connection with an external power source. The movable housing 804 is connected to the fixed housing 802 through a mechanical joint 806. The movable housing 804 includes a plurality of light sources 810, a motor 812, an adjustment lens 814, a camera unit 816, a memory unit 818, and a controlling unit 820 connected to

TABLE

| Name | Abbreviation | Wavelength(nm) | Photon energy (eV, aJ) | Property |
| --- | --- | --- | --- | --- |
| Ultra Violet-A | UVA | 315-400 | 3.10-3.94 (0.497-0.631) | Long-wave, black light, not absorbed by the ozone layer |
| Ultra Violet-B | UVB | 280-315 | 3.94-4.43 (0.631-0.710) | Medium-wave, mostly absorbed by the ozone layer |
| Ultra Violet-C | UVC | 100-280 | 4.43-12.4 (0.710-1.987) | Short-wave, germicidal, completely absorbed by the ozone layer and atmosphere |
| Near-Ultra Violet | NUV | 300-400 | 3.10-4.13 (0.497-0.662) | |
| Middle-Ultra Violet | MUV | 200-300 | 4.13-6.20 (0.662-0.993) | |
| Far-Ultra Violet | FUV | 122-200 | 6.20-12.4 (0.993-1.987) | |
| Hydrogen Lyman-alpha | H Lyman-α | 121-122 | 10.16-10.25 (1.628-1.642) | Spectral line at 121.6 nm, 10.20 eV. Ionizing radiation at shorter wavelength |

According to an advantageous embodiment of the present disclosure, the UV illumination device (200, 700) can fit into the existing light bulb holder and tube light holder.

According to an advantageous embodiment of the present disclosure, the UV illumination device (200,700) can automatically sense the human or living organism's presence by using sensors and can act as normal LED light and illuminate light through the plurality of LEDs 240.

According to an advantageous embodiment of the present disclosure, the UV illumination device (200, 700) can automatically detect the microorganisms and items subjected to disinfect and illuminates UV light corresponding to their parameters.

According to an advantageous embodiment of the present disclosure, the memory unit 140 stores the information of the camera unit 816 and the memory unit 818. The controlling unit 820 includes a processor configured to perform the following steps including initiating the camera unit 816 to scan at least one item within an enclosed area; storing a scanned data of said item in the memory unit 818; identifying said item from the scanned data; rotating shaft 824 of the motor 812 which in turn facilitates the rotation of the UV light projecting from said plurality of light sources 810; illuminating UV light on the at least one item identified from the scanned data; projecting the UV light on the at least one item; providing a back and forth movement to the adjustment lens 814 with respect to the plurality of light sources 810 using the motor and adjusting the UV light illuminated on the at least one item. The adjustment of UV illuminated light can be either manual or automatic.

The adjustment lens 814 can be a convex or concave lens depending on the application of the incident UV light beam falling on the item for sterilization. Let's assuming if the direction of UV light is to be adjusted in such a manner that the nature of light is converging, or the light needs to converge over the item in a way that, multiple UV lights beams need to converge at an area or intersect at a particular angle thereby projecting on an item per the requirements of the user, then in that example scenario convex lens is used. Here the focal length of the convex lens used as the adjustment lens 814 will be positive. Now take another example scenario where multiple UV ray are diverging or the light needs to diverge over the item or area in a way that, multiple UV lights diverge from the item at a particular angle thereby projecting the light beam as per the requirements of the user, then in that example scenario concave lens is used. Here the focal length of the convex lens used as the adjustment lens 814 will be negative. The adjustment lens 814 allows the device 800 to cover or project the light in maximum area in an enclosed structure, more precisely the adjustment lens 814 added more coverage to the light projection with the ball socket movement.

The plurality of light sources 810, the camera unit 816, the memory unit 818, and the controlling unit 820 are mounted on a base plate 830. The mechanical joint 806 is attached to a support surface 826 in a rotatable manner. The movable housing 804 further includes a transparent cover 804 to cover the base plate 830, the base plate 830 mounted on the support surface 826. The mechanical joint 806 also includes a socket 806A accommodating a ball 806B in a manner that the ball can rotate in any desired direction within the socket. The plurality of light sources 810 could be a plurality of light-emitting diode (LED), laser lights, or any other light sources which can produce light in the UV range.

The UV illumination device is not intended to be limiting to a ball-socket mechanism but also utilizes other mechanisms such as locking joint mechanism, hinge mechanism, spherical rolling joint mechanism, or any other locking mechanism. The locking joint mechanism involves placing a latch between two joints. The rotation of the ball 806B of the movable housing 804 is achieved using the same latch which locks the ball 806B by engaging with the ball 806B via an electromagnetic force. This locking joint mechanism utilizes the principle of mechanical coupling. The hinge mechanism involves the use of different hinges that rotates the ball 806B about a fixed axis of rotation, due to the engagement of hinges with the ball 806B directly or indirectly, thereby securing the ball 806B at a fixed position. The spherical joint mechanism involves the use of spherical bearings i.e., ball bearings used with the joints to engage the ball 806B facilitating the ball 806B to rotate around its axis.

According to an alternate embodiment of the present disclosure, the processor (not shown) of the controlling unit 820 allows a back and forth movement of the adjustment lens 814 with respect to the plurality of light sources 810 using the motor 812 and adjust the UV light illuminated on the at least one item. The processor can be programmed using software executable code in the form of instructions stored in the memory unit 818. The device and methods disclosed herein can be implemented in hardware, software, firmware, or a combination thereof. The software can include computer-readable instructions stored in memory (e.g., non-transitory, tangible memory, such as solid-state memory (e.g., ROM, EEPROM, FLASH, RAM), optical memory (e.g., a CD, DVD, Blu-ray disc, etc.), magnetic memory (e.g., a hard disc drive), etc.), configured to implement the algorithms on a general-purpose computer, one or more special-purpose processors, or combinations thereof. For example, one or more computing devices, such as a processor, may execute program instructions stored in computer readable memory to carry out processes disclosed herein. Hardware may include state machines, one or more general-purpose computers, and one or more special-purpose processors. While certain types of device configurations and methods are described herein for illustrative purposes, other types of device configurations and methods may be used.

According to an alternate embodiment of the present disclosure, the UV illumination device 800 can utilize another rotation mechanism e.g., cam mechanism, gear mechanism, or any other suitable rotation mechanism.

According to an alternate embodiment of the present disclosure, the UV illumination device comprises of a PCB assembly 828 installed above the base plate 830 on which the plurality of light sources 810, the motor 812, the camera unit 816, the memory unit 818, and the controlling unit 820 are mounted. The adjustment lens 814 is mounted on a lead screw 832 that is connected to the motor 812 through a motor spindle 824. The Adjustment lens 814 can move back and forth on the lead screw 832 with the help of the motor rotation. The rotation of the motor 812 and the movement of the device 800 can be controlled through a remote device.

According to an alternate embodiment of the present disclosure, a mirror reflector can be positioned at any bottom portion or surface for example a floor to target the surfaces which can't be covered from the direct projection of UV illumination while the device 800 is mounted or fixed on the ceiling or top of an enclosure. The UV illumination device 800 as disclosed in the present invention utilizes various communication modules like object detection module, localization module, machine learning module, and artificial intelligence module through controlling unit 820 to identify an object and determine the angle to which the mirror reflector needs to be positioned on the floor. Once the information for the positioning angle of the mirror reflector with respect to the device 800 is determined, it is received by the user's remote device. The user then adjusts the mirror reflector by himself using the remote device in order to project the UV light on the surface underneath the identified object. The surface underneath the identified object could be under the table, under the bed, or any surface where the UV illumination device cannot reach directly from the top. The mirror reflector used in the UV illumination device of the present invention is of spherical shape, but not intended to be limiting to the spherical shape. The shape of the mirror reflector can be flat, spherical, parabolic, or any other shape. A parabolic mirror reflector is a reflective surface projecting UV light on at least one item or object. A flat mirror reflector is not necessarily flat at times nor are they always highly reflective.

Figure 10:
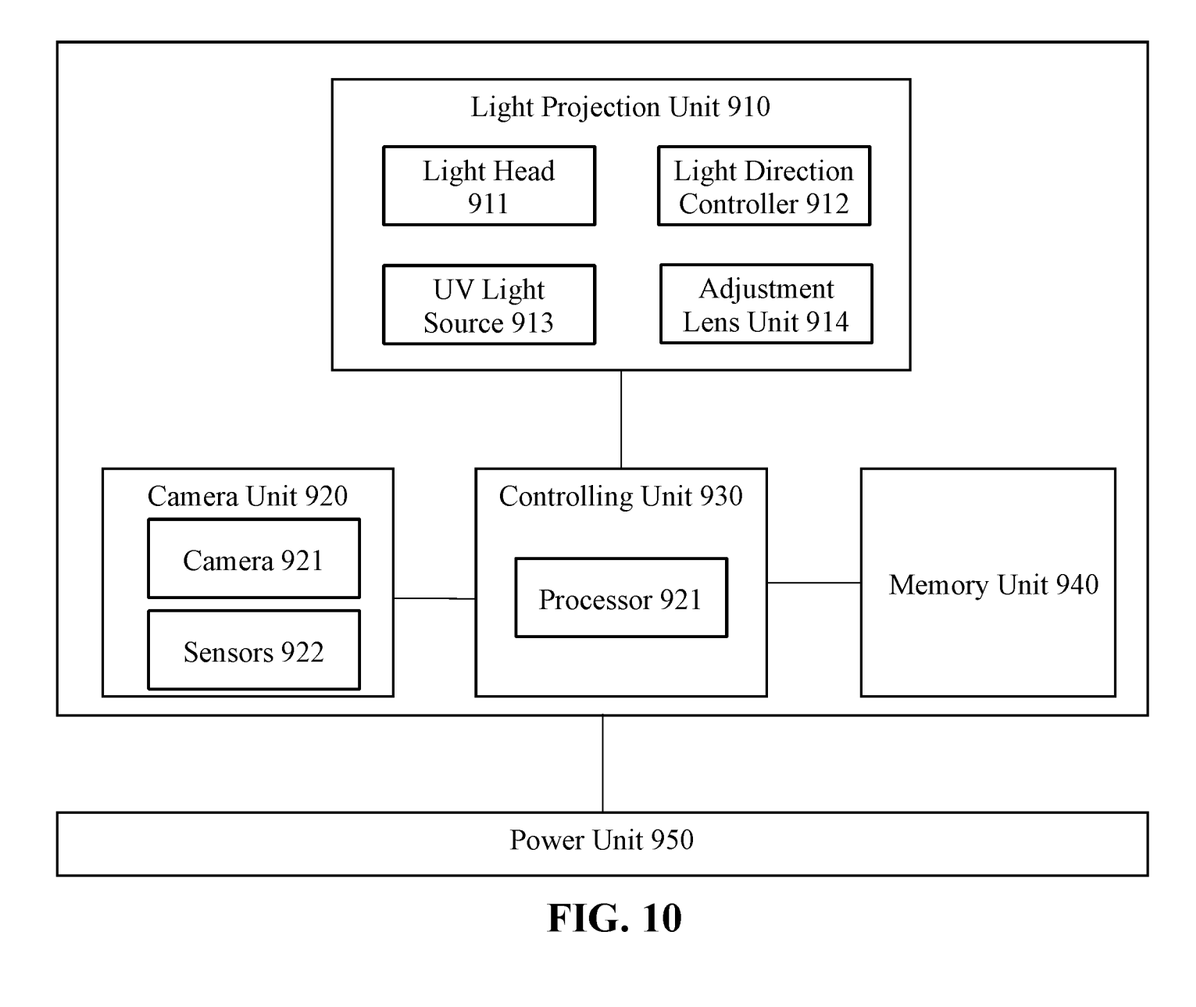

FIG. 10 shows a block diagram of a UV illumination device 900 according to an alternate embodiment of the present disclosure. The UV illumination device 900 includes a light projection unit 910, a camera unit 920, a controlling unit 930 a memory unit 940, and a power unit 950. Further, the light projection unit 910 includes a light head 911, a light direction controller 912, a UV light source 913, and an adjustment lens unit 914. The UV light source 913 is adapted to project the UV light (not shown) on the light direction controller 912, thereafter the light direction controller 912 directs the UV light in the desired direction through the light head 911. Lastly, the adjustment lens unit 914 comprises a plurality of spherical lenses which move back and forth with respect to the plurality of light 810 sources, due to the rotation of the motor 812 by the controlling unit 930 and adjusting the UV light illuminated on the at least one item.

The UV illumination device 900 uses a mirror galvanometer as the light direction controller. In this, the galvanometer consists of a coil that is suspended by means of silken threads. At least one mirror is attached to at least one coil. The light from the light source is made to fall on one mirror. The reflected light will fall on a light head 911 to project the light on the desired area.

The controlling unit 930 is electronically and communicatively coupled to the light projection unit 910, the memory unit 940, the camera unit 920, and the power unit 950. In this, the processor 931 is adapted to control the light projection unit 910 based on the camera unit 920 inputs.

The adjustment lens 814 though concave or convex by nature depending on the light application to be achieved may be plano-concave, plano-convex, convex-concave, meniscus lens or any other lens configuration According to an alternate embodiment of the present invention, the UV illumination device also comprises a temperature sensor, a motion sensor and an IR sensor to detect the body temperature of the human body, detecting the motions of various objects in the enclosed area and signlaing the user on a remote device connected through a wired or wireless mean to the said device. Further, the controlling unit is also configured to receive the image of the item or the surface to be sterilized. The controlling unit is configured to use the image data of the item or the surface as output, and inputs feedback regarding if the item or the surface to be cleaned is sterilized properly or not, based on the image data of the item or the surface obtained through the camera and the sensors in the camera unit.

In accordance to an alternate embodiment of the present invention, there can be a possibility of usage of the plurality of illumination devices for illuminating light on the at least one item or surface. The intensity of UV light emitted by UV illumination devices can be controlled by the controlling unit in a manner, that if one UV illumination device is selected as the leading illumination device, then control of other UV illumination devices is managed by the leading illumination device. In other words, this case or example is more of a master-slave mode where the UV illumination device selected as the leading illumination device is a "Master illumination device" and the other UV illumination devices which are getting controlled due to the leading device are called "Following illumination devices" as they are being controlled by the Master illumination device. The following illumination devices are in synchronization with each other or the master illumination device through Wi-Fi (Wireless Fidelity), Bluetooth, ZigBee or any other communication approach.

Certain embodiments ofthis invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although specific embodiments and certain structural arrangements have been illustrated and described herein, it will be clear to those skilled in the art that various other modifications and embodiments may be made incorporating the spirit and scope of the underlying inventive concepts and that the same is not limited to the particular methods and structure herein shown and described except in so far as determined by the scope of the appended claims.

What I claim is:

1. An Ultra-Violet (UV) illumination device used for sterilization of any item or area, the UV illumination device comprising:
    a fixed housing including a base, the base comprises a pair of electrical terminals establishing a connection with an external power source;
    a movable housing connected to the fixed housing through a mechanical joint, wherein the movable housing includes:
        a plurality of light sources, a camera unit, and a memory unit mounted on a base plate,
        a motor,
        an adjustment lens, and
        a controlling unit connected to the camera unit and the memory unit, wherein the controlling unit includes a processor with computer-implemented code stored as instructions in the memory unit, the instructions configuring the processor to perform:
            scanning of at least one item within an enclosed area, by the camera unit,
            storing scanned data of the at least one item in the memory unit,
            identifying the at least one item from the scanned data,
            rotating of the motor, facilitating rotation of the UV illumination device,
            illuminating UV light on the at least one item identified from the scanned data,
            projecting the UV light on the at least one item,
            providing back and forth movement to the adjustment lens with respect to the plurality of light sources using the motor, and
            adjusting the UV light illuminated on the at least one item.

2. The UV illumination device of claim 1, wherein the mechanical joint is a ball socket joint attached to a support surface in a rotatable manner and a socket of the ball socket joint accommodates the ball in a manner that the ball can rotate in any desired direction within the socket.

3. The UV illumination device of claim 1, wherein the plurality of light sources is selected from a group consisting of a plurality of light emitting diode (LED), laser lights, or any other light sources which can produce light in the UV range.

4. The UV illumination device of claim 1, wherein the camera unit comprises a plurality of sensors.

5. The UV illumination device of claim 1, further comprising an object detection module, a machine learning module, a localization module, and an artificial intelligence module in order to identify the at least one item.

6. The UV illumination device of claim 1, wherein the UV illumination device is adapted to illuminate light of visible portion of the electromagnetic spectrum, in presence of a user within the enclosed area.

7. The UV illumination device of claim 1, wherein the UV illumination device is adapted to illuminate the at least one UV light beam in absence of a user within the enclosed area.

8. The UV illumination device of claim 1, wherein the enclosed area is selected from a group consisting of a bathroom, a toilet, a room, a lift, an operation theater or any other closed structure.

9. The UV illumination device of claim 1, wherein the UV illumination device is capable of rotating with the help of a rotation assembly.

10. The UV illumination device of claim 1, wherein the user can control shape, time and intensity of the UV light beam by using a remote device.

11. The UV illumination device of claim 1, wherein the illumination device comprises a mirror reflector positioned in the path of light beam to deviate the light beam.

12. The UV illumination device of claim 1, wherein the controlling unit is configured to process the image data to determine whether a surface needs to be disinfected or not.

13. The UV illumination device of claim 1, wherein the illumination device comprises a UV sensor to identify the microorganisms including microbes and mites present in the item or the area to be sterilized and upon the identification of the microorganisms acting on any item or the area, detecting intensity of incident UV radiation to be illuminated on the microorganisms to eliminate the microorganisms pests.

14. The UV illumination device of claim 1, wherein the UV illumination device is further adapted to sterilize or disinfect underwater.

15. The UV illumination device of claim 1, wherein the UV illumination device works in master-slave mode.

* * * * *